United States Patent [19]

Hohki et al.

[11] Patent Number: 4,682,040
[45] Date of Patent: Jul. 21, 1987

[54] IMAGE PICKUP APPARATUS FOR A PRINTED WIRING BOARD

[75] Inventors: Tetsuo Hohki; Tetsuo Sano, both of Kyoto; Eiji Kodama, Higashi-Osaka; Hisayuki Tsujinaka, Kyoto, all of Japan

[73] Assignee: Dainippon Screen Mfg. Co., Ltd., Kyoto, Japan

[21] Appl. No.: 730,797

[22] Filed: May 6, 1985

[30] Foreign Application Priority Data

Jun. 2, 1984 [JP] Japan .................. 59-113628

[51] Int. Cl.$^4$ ..................... G01N 21/47; G01N 21/55; G01N 21/89
[52] U.S. Cl. ..................... 250/571; 250/572; 356/445; 356/446
[58] Field of Search ................ 250/571, 572; 356/445, 356/446, 448, 447, 371

[56] References Cited

U.S. PATENT DOCUMENTS

| | | | |
|---|---|---|---|
| 3,771,956 | 7/1973 | Jakeman et al. | 250/571 |
| 3,892,492 | 7/1975 | Eichenberger | 356/446 |
| 4,276,910 | 7/1981 | Eichenberger | 250/571 |
| 4,330,712 | 5/1982 | Yoshida | 250/572 |
| 4,525,630 | 6/1985 | Chapman | 356/446 |

FOREIGN PATENT DOCUMENTS 0053992 6/1982 European Pat. Off. ............ 356/446

Primary Examiner—Edward P. Westin
Assistant Examiner—Charles Wieland
Attorney, Agent, or Firm—Brumbaugh, Graves, Donohue & Raymond

[57] ABSTRACT

Disclosed herein is an image pickup apparatus for a printed wiring board comprising a solid state image sensor whose light receiving surface is set to be opposed to the surface of the printed wiring board, a main illumination source arranged to satisfy the law of regular reflection on the surface of the printed wiring board with respect to the light receiving surface of the solid state image sensor and a subsidiary illumination source arranged not to satisfy the law of regular reflection with respect to the light receiving surface of the solid state image sensor thereby to supply the light receiving surface with scattering light by strias formed on copper patterns. The amount of regularly reflected light, which is changed depending on the strias formed on the copper patterns, is substantially compensated by the scattering light, so that the amounts of light received by the solid state image sensor relating to the copper patterns are made substantially constant regardless of the radiation pattern of the strias. In addition, the main and subsidiary illumination sources are formed by light emitting diodes thereby to attain technical and economical advantages.

12 Claims, 17 Drawing Figures

Fig. 5
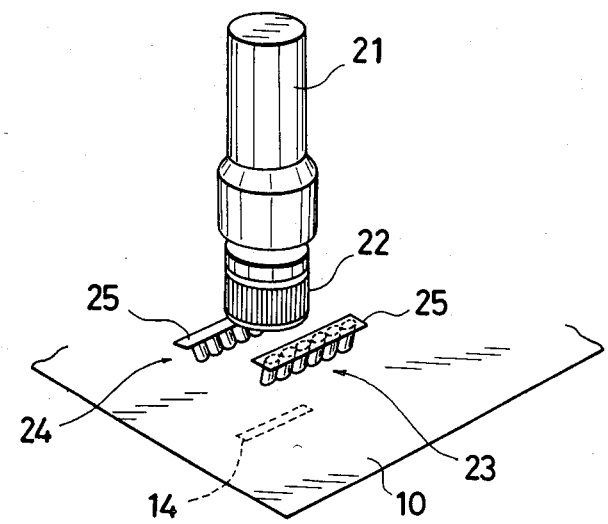
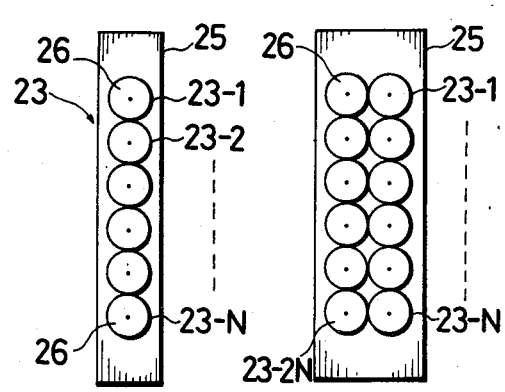
Fig. 6a  Fig. 6b  Fig. 7a  Fig. 7b

RADIATION PATTERN

IMAGE PICKUP APPARATUS FOR A PRINTED WIRING BOARD

BACKGROUND OF THE INVENTION

1. Field of the Invention

The present invention relates to an image pickup apparatus employed in a device for automatically performing visual inspection of wiring patterns of a printed wiring board, and more particularly, it relates to improvement in an illumination system for illuminating the printed wiring board.

2. Description of the Prior Art

In general, a printed wiring board is formed by a laminated plate member covered by copper foil. The copper-covered laminated plate member is polished in advance to etching processing by passage through, e.g., a buffing roller. Such buffing operation is so performed that a photoresist film is effectively adhered to the copper-covered laminated plate member and the surface of the copper foil is activated, thereby to smoothly perform the etching processing. After the etching processing, the photoresist film is removed. Copper patterns thus formed have flaws caused by the buffing operation on the surfaces thereof, which flaws define strias substantially in the same direction with respect to the printed wiring board. The directions of such strias are not necessarily identical with respect to printed wiring boards of the same kind.

FIG. 1 is a partially fragmented perspective view of a printed wiring board. A printed wiring board 3 which comprises a copper pattern 1 having substantially V-shaped strias 2 is subjected to successive image pickup in defect inspection of wiring patterns by an image pickup apparatus. Illumination light 4 is irradiated on the surface of the printed wiring board 3, so that light 5 reflected by the surface of the printed wiring board 3 is received in image pickup means, e.g., a solid state image sensor (not shown) through a lens (not shown). The solid state image sensor, which serves as the image pickup means, outputs image pickup signals in response to the amount of received light. A substrate base portion 6 and the copper pattern 1 are discriminated from each other on the basis of the image pickup signals, whereby information is obtained as binary picture images. Thus, it is necessary to facilitate such discrimination in the signal processing system by making the copper pattern 1 as the object of image pickup sufficiently different in reflected light amount from the substrate base portion 6 as the background.

However, since the copper pattern 1 has the strias 2 on its surface, the illumination light 4 is diffusedly reflected by the strias 2. The extent of the diffused reflection depends on relation between the direction of irradiation of the illumination light 4 and the direction of the strias 2, and hence the reflected light on the copper pattern 1 and that on the substrate base portion 6 are not necessarily in fine contrast. In other words, the strias 2 appear in various directions even on printed wiring boards of the same kind, and hence the amount of light reflected in specific directions such as a regularly reflected direction and the direction of setting of the image pickup means is changed at considerable rate depending on the direction of the strias 2, assuming that the illumination light 4 is irradiated in a constant direction. Since the amount of reflected light from the substrate base portion 6 is constant in any desired portion and on printed wiring boards of the same kind, the contrast is changed depending on the direction of the strias 2, i.e., depending on the printed wiring boards. Such changes in contrast cannot be effectively absorbed if discriminativity in the signal processing system is not sufficiently highly increased, particularly when pattern data of printed wiring boards are to be compared in pixel unit with each other.

Improvement in discriminativity in the signal processing system leads to remarkable increase in cost. Therefore, the aforementioned changes in contrast have generally been covered by extremely high-powered illumination so that image pickup signals relating to copper patterns are sufficiently detected even if the amount of reflected light from the copper patterns is at the minimum value. Such high-powered illumination is generally performed by tungsten or halogen lamps. However, the high-powered illumination employing the tungsten or halogen lamps has the following disadvantages:

In the first place, there is a problem of heat generation, such that the lamp generates a large quantity of heat by the high-powered illumination. Since a signal processing circuit is arranged in the vicinity of the lamp, significant thermal influence is exerted not only on a solid state image sensor but on respective parts of the circuit, such that, e.g., the dark current of the solid state image sensor is increased by increase in the ambient temperature. Further, in order to prevent such thermal influence, arrangement of the mechanical portion, the circuitry portion and the like must be specifically designed or a large-scale mechanism is required for heat generation.

In the second place, the lamp itself has such a problem that it must be large-sized for performing high-powered illumination, leading to increase in volume of the entire device. Further, the lamp is mechanically weak, relatively undurable, considerably defective in stability of the luminous power and inconvenient to handle.

SUMMARY OF THE INVENTION

Accordingly, a principal object of the present invention is to provide a novel image pickup apparatus for a printed wiring board which overcome changes in the amount of reflected light caused by radiation pattern of strias on copper patterns simply without employing a light source having high luminous power.

Another object of the present invention is to provide an image pickup apparatus for a printed wiring board which is small sized and convenient to handle.

Still another object of the present invention is to provide an image pickup apparatus for a printed wiring board in which optical characteristics of a solid state image sensor and/or an illumination source as image pickup means are improved thereby to improve the signal-to-noise ratio of image pickup signals.

A further object of the present invention is to provide an image pickup apparatus for a printed wiring board which is simplified in design and reduced in cost.

In order to attain the aforementioned objects, the present invention is characterized in that an image pickup apparatus for a printed wiring board comprises illumination source means for supplying irradiated light on the surface of a printed wiring board formed with copper patterns and a solid state image sensor for receiving light reflected by the surface of the printed wiring board thereby to output image pickup signals. A light receiving surface of the solid state image sensor is set in an opposite manner to the surface of the printed wiring board and the illumination source means is formed by a main illumination source arranged to satisfy the law of regular reflection on the surface of the printed wiring board with respect to the light receiving surface of the solid state image sensor and a subsidiary illumination source arranged not to satisfy the law of regular reflection with respect to the light receiving surface of the solid state image sensor thereby to supply the light receiving surface with scattering light by strias formed on the surfaces of the copper patterns. The amount of reflected light from the surfaces of the copper patterns by the main illumination source which is reduced by the strias of the copper patterns in comparison with the amount of reflected light on a substrate base portion is substantially compensated by the scattering light by the subsidiary illumination source, whereby the amount of reflected light is maintained at a high value and substantially stabilized with respect to changes in the direction of the strias.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a roughly illustrated perspective view showing another embodiment of the present invention, which employs light emitting diodes in an illumination source;

FIGS. 6a and 6b are roughly illustrated plan views of light emitting diode arrays employed as illumination sources;

FIGS. 7a and 7b are roughly illustrated plan views of light emitting diode arrays integrally formed as illumination sources;

DESCRIPTION OF THE PREFERRED EMBODIMENTS

Figure 2A:
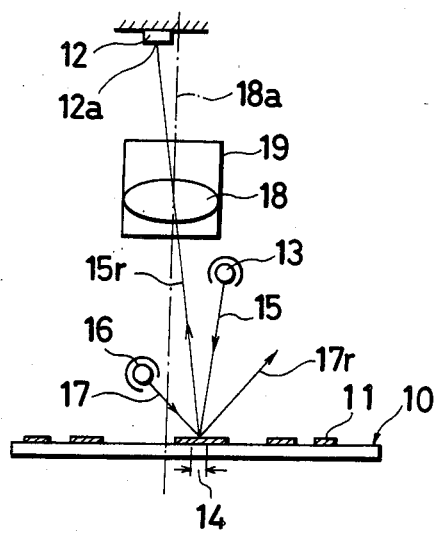
FIGS. 2a and 2b are roughly illustrated sectional side views respectively showing embodiments of the present invention.

Referring to FIG. 2a illustrating an embodiment of the present invention, reference numeral 10 indicates a printed wiring board arranged on a prescribed base plate (not shown), which printed wiring board 10 is provided with copper patterns 11. Numeral 12 depicts a solid state image sensor which is adapted to perform image pickup of the copper patterns 11, and is formed by a one-dimensional CCD image sensor. The one-dimensional CCD image sensor 12 extends in a perpendicular manner in FIG. 2a over the printed wiring board 10, so that a light receiving surface 12a thereof is set in parallel with the surface of the printed wiring board 10. Numeral 13 depicts a straight type tungsten lamp having relatively small luminous power, which functions as a main illumination source for supplying irradiated light 15 to a rectangular image pickup region 14 extending in a perpendicular manner in FIG. 2a. The straight type tungsten lamp 13 is arranged in parallel with the one-dimensional CCD image sensor 12 in such a position that satisfies the law of regular reflection with respect to the light receiving surface 12a. Numeral 16 depicts another straight type tungsten lamp having relatively small luminous power, which functions as a subsidiary illumination source and extends in parallel with the straight type tungsten lamp 13 positioned thereover, for similarly supplying irradiated light to the image pickup region 14. The straight type tungsten lamp 16, serving as the subsidiary illumination source, is arranged in such a position that will not satisfy the law of regular reflection with respect to the light receiving surface 12a of the one-dimensional CCD image sensor 12, i.e., a position in which geometical regularly reflected light 17r obtained by reflection of the irradiated light 17 on the surface of the printed wiring board 10 is not incident upon the light receiving surface 12a. Numeral 18 depicts an image pickup lens fixed to a lens mount 19, whose optical axis 18a is set to be in parallel with a normal line on the surface of the printed wiring board 10, thereby to perform formation of the image on the image pickup region 14 on the light receiving surface 12a of the one-dimensional CCD image sensor 12.

The irradiated light 15 from the tungsten lamp 13 serving as the main illumination source is reflected, including diffused reflection, by the image pickup region 14, so that regularly reflected light 15r and part of diffusedly reflected scattering light are incident upon the light receiving surface 12a of the one-dimensional image sensor 12. On the other hand, the light 17 irradiated from the tungsten lamp 16 serving as the subsidiary illumination source is so reflected by the image pickup region 14 that regularly reflected light 17r thereof escapes in a direction completely irrelevant to the image pickup operation while part of diffusedly reflected scattering light is incident upon the light receiving surface 12a of the one-dimensional image sensor 12 through the image pickup lens 18.

When, in a fixed image pickup apparatus in which the printed wiring board 10 is moved, copper patterns are introduced into the image pickup region 14, both of the irradiated light 15 and 17 are regularly or diffusedly reflected depending on the direction of strias thereof. If the direction $\theta$ of the strias is perpendicular to the direction in which the tungsten lamps 13 and 16 extend, i.e., $\theta = 90°$, the copper patterns substantially present the state of a mirror face (regular reflection) thereby to minimize the extent of diffused reflection. However, when the said direction $\theta$ is in parallel with the strias, i.e., $\theta = 0°$, the copper patterns are greatly influenced by the strias whereby diffused reflection of the incident light is maximized.

Figure 3:
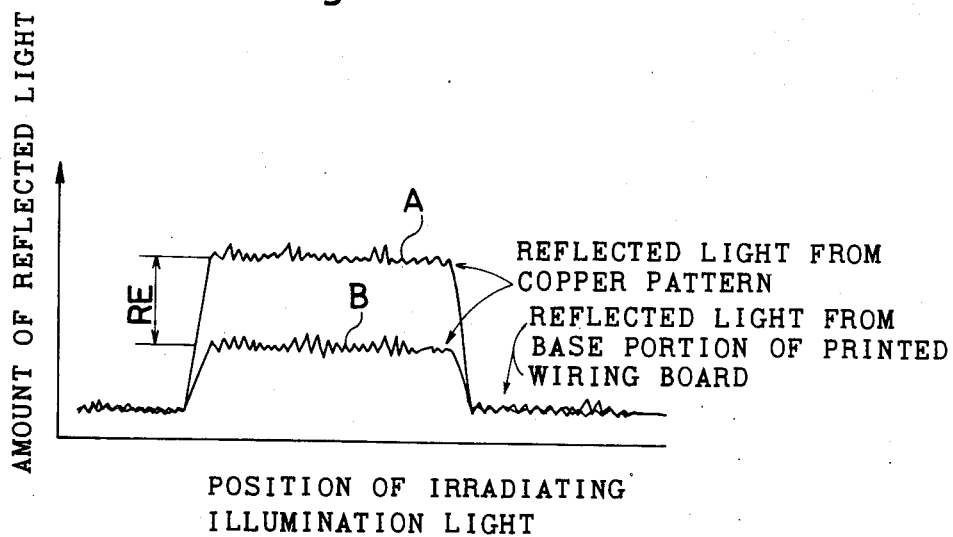
FIG. 3 illustrates a manner in which the amount of reflected light from a main illumination source is changed by strias formed on the surfaces of copper patterns.
Figure 4:
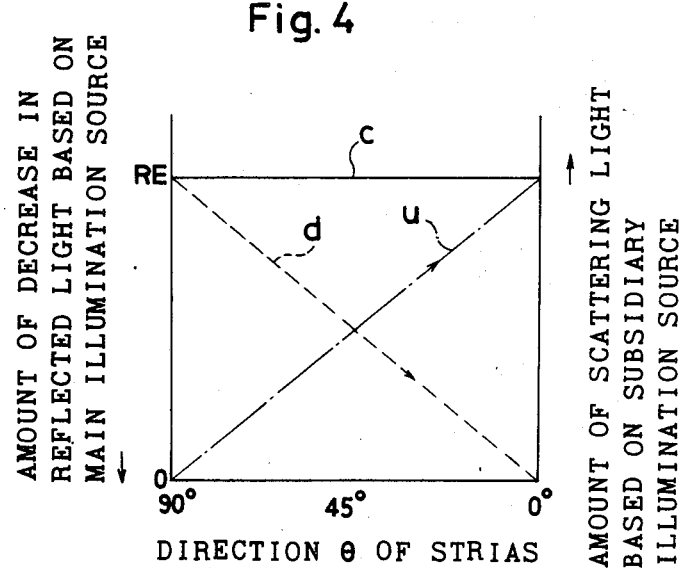
FIG. 4 is a graph showing the principle of the present invention.

Assuming that the direction $\theta$ is equal to 90°, substantially the regularly reflected light 15r alone is incident upon the light receiving surface 12a, and diffused reflection components can practically be disregarded. A waveform A in FIG. 3 shows distribution of the amount of the light 15r regularly reflected by the copper patterns. On the other hand, when the direction $\theta$ is equal to 0°, the irradiated light 15 is diffusedly reflected at the maximum by the strias of the copper patterns, whereby the amount of the regularly reflected light 15r is considerably decreased. A waveform B in FIG. 3 shows distribution of the amount of the light obtained by the copper patterns at this time. Difference RE between the both light amount distribution levels is substantially continuously changed as the characteristic line d in FIG. 4, owing to the direction $\theta$ of the strias of the copper patterns.

Figure 1:
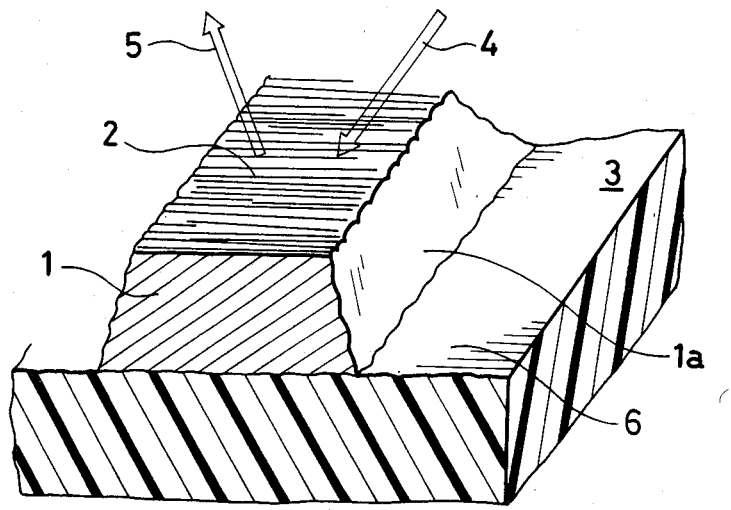
FIG. 1 is a partially fragmented perspective view showing structure of a printed wiring board.

In contrast to the above, the diffused reflection components are obtained at the minimum amount with respect to both of the main and subsidiary illumination sources 13 and 16 in the case where the direction $\theta$ is equal to 90° as hereinabove described, and the amount of the scattering light thereof incident upon the light receiving surface 12a may practically be disregarded. However, in the case where the direction $\theta$ is equal to 0°, the irradiated light 17 from the subsidiary illumination source 16 is diffusedly reflected at the maximum, whereby the scattering light thereof is incident upon the light receiving surface 12a. In other words, in case of $\theta = 0°$, the irradiated light 15 from the main illumination source 13 is so greatly diffusedly reflected that the scattering light thereof is incident upon the light receiving surface 12a, whereas the amount of the regularly reflected light 15r is so largely decreased that the total amount of the light incident upon the light receiving surface 12a is considerably degreased, while the irradiated light 17 from the subsidiary illumination source 16 is also greatly diffusedly reflected whereby the amount of scattering light components incident upon the light receiving surface 12 is increased by increase in the amount of the scattering light thereof, and hence the decrease in the amount of the regularly reflected light 15r is substantially compensated by the said scattering light. In the present embodiment, the set position and the set angle of the subsidiary illumination source 16 and luminance of the light source are so selected that the compensation light amount of the scattering light by the subsidiary illumination source 16 is approximate to the characteristic line u in FIG. 4. Therefore, synthetic characteristics c thereof correspond to the substantially constant value RE. Consequently, the light amount level by the copper patterns is substantially similar to the waveform A in FIG. 3 regardless of the direction $\theta$ of the strias in the copper patterns. In other words, the reflection factor of the substrate base portion 6 (see FIG. 1) is substantially constant at any desired portion, and hence the contrast with respect to the amount of the reflected light from the substrate base portion 6 and the copper patterns 11 of the printed wiring board 10 can be maintained at a substantially constant high value in any portion.

Figure 2B:
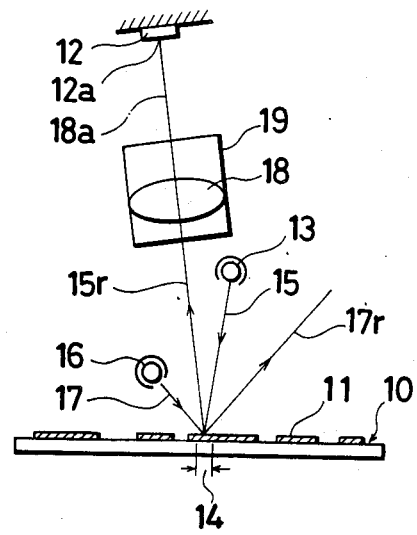

FIG. 2b shows another embodiment of the present invention.

In FIG. 2b, numerals identical to those in FIG. 2a indicate the same or corresponding components, and detailed explanation thereof is herein omitted. The embodiment as shown in FIG. 2b is different from that of FIG. 2a in arrangement of the image pickup lens 18 and the one-dimensional CCD image sensor 12. Namely, although the one-dimensional CCD image sensor 12 is in the device as shown in FIG. 2a in offset relation to the optical axis 18a of the pickup lens 18, such one-dimensional CCD image sensor 12 is generally contained in a cylindrical lens mount to be coupled with the lens mount 19 of the image pickup lens 18 as a CCD camera. Thus, in the device as shown in FIG. 2b, an image pickup lens 18 is so arranged that its optical axis 18a is coincident to the optical path of regularly reflected light 15r from a main illumination source 13 while a one-dimensional CCD image sensor 12 is so arranged that a normal line on a light receiving surface 12a is coincident to the optical axis 18a, whereby the device is brought in the aforementioned standard arrangement.

By virtue of such arrangement, the regularly reflected light 15r is incident upon the light receiving surface 12a in a vertical manner thereby to improve photoelectric conversion efficency, as well as simplifying design of the device and the mechanism thereof.

In each of the aforementioned embodiments as shown in FIGS. 2a and 2b, the incident angle of the irradiated light 15 from the main illumination source 13 to the printed wiring board 10 is selected to be 4°. Such selection is made, as clearly understood from FIG. 1, so that the copper patterns 1 are in trapezoidal cubic structure with respect to the flat surface of the substrate base portion 6, thereby to eliminate influence exerted by the shoulder portion 1a as the inclined surface thereof, i.e., the influence exerted by roughness of the surface and by inclination by about 15° against a normal line on the surface of the printed wiring board 10, to the utmost for efficiently obtaining information of two-dimensional patterns. The said incident angle is not restricted to 4° and may preferably be smaller than the said value, while no bad influence is substantially exerted on image pickup outputs within a range up to 10°.

In the aforementioned embodiments, the main and subsidiary illumination sources are both implemented by the tungsten lamps having small luminous power. According to the substance of the present invention, the illumination sources are not required to perform such high-powered illumination as in the conventional device, and may simply have illuminance in response to characteristics of the solid state image sensor. However, since the illumination sources are formed by the tungsten lamps which are adapted to convert electric currents into heat and then convert the heat into light, there inevitably rises a problem of heat generation. In addition, the tungsten lamps are relatively large-sized whereby the size of the image pickup apparatus is inevitably increased, leading to problems of supporting structure therefor and vibration resistance thereof particularly in case of movement. With respect to the characteristics of the tungsten lamp itself, the luminous power is instably subjected to age-based changes and the life of the lamp is relatively short, leading to difficulty in handling such as indispensability in operation for replacement.

Accordingly, the following embodiment is adapted to improve the illumination sources employed in the aforementioned embodiments, thereby to overcome the disadvantages of heat generation regarding the illumination sources as well as to simplify handling of the illumination sources by making the same small-sized, light-weight and durable, while facilitating signal processing.

For attaining the aforementioned objects, illumination sources are formed by a plurality of light scattering type diodes arranged in alignment in a more preferable embodiment of the present invention. More preferably, the said light emitting diodes are of bright type for securing high illuminance. Further preferably, the peak of spectral sensitivity of a solid state image sensor is selected to be in a long-wavelength (partially including near infrared rays) side of visible light in compliance with spectral reflection characteristics of copper patterns, while the peak of spectral light emission intensity of the said light emitting diodes is also selected in the long-wavelength (partially including near infrared rays) side of the visible light in compliance with the spectral reflection characteristics of the copper patterns. By virtue of such structure, image pickup patterns can be taken in further improved contrast with respect to the background.

FIG. 5 shows a roughly illustrated perspective view showing the said embodiment, in which numeral 21 indicates the so-called CCD camera containing a one-dimensional CCD image sensor, numeral 22 indicates an image pickup lens coupled with the CCD camera 21, numeral 23 indicates a light emitting diode array light source serving as a main illumination source and numeral 24 indicates a light emitting diode array light source serving as a subsidiary illumination source. Numeral 25 indicates a circuit substrate to which the light emitting diode elements are mounted.

Figure 8:
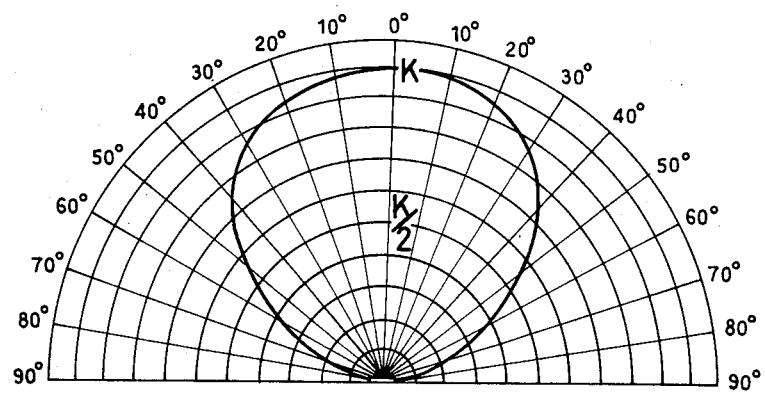
FIG. 8 is a graph showing the radiation pattern of a light scattering type light emitting diode employed in the embodiment of the present invention.
Figure 8:
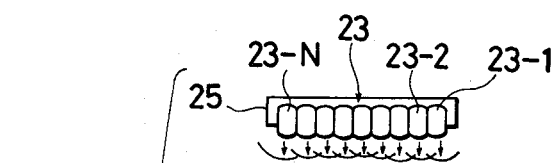

Description is now made on the light emitting diode array light sources 23 and 24, which serve as illumination sources. The light emitting diode is hereafter referred to as LED, and the following description is made on the LED array light source 23, since the LED array light sources 23 and 24 are identical in structure to each other. As shown in FIG. 6a in typical plan view, the LED array light source 23 is formed by a plurality of single-unit LED elements 23-1, 23-2, ..., 23-N aligned in close contact with each other to be fixed to a substrate 25, and the entire length N thereof is determined in correspondence to the length of an image pickup region 14. Each of the LED elements 23-1, 23-2, ..., 23-N is formed by the so-called light scattering type LED element obtained by mounting a semiconductor chip on a stem and molding the same by transparent resin 26 containing a light scattering agent. FIG. 8 shows the radiation pattern thereof, which is broad and symmetrical about the axis of 0°.

Figure 9A:
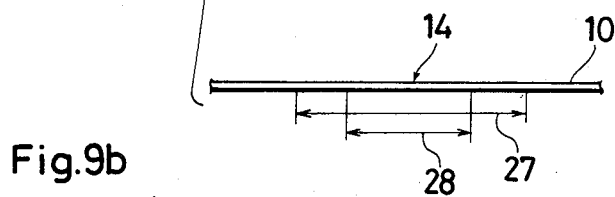
FIGS. 9a and 9b are diagrams for illustrating that an image pickup region may be supplied with uniform illuminance distribution by a scattering type light emitting diode array light source.
Figure 9B:
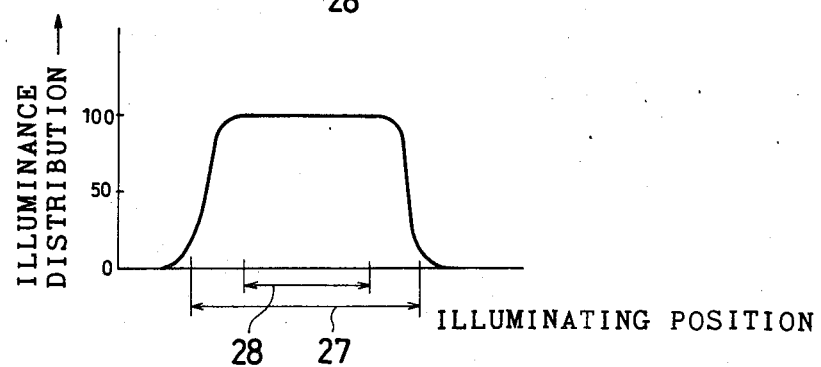

The LED elements having such radiation pattern are aligned in an array to be applied to the illumination source, thereby to supply substantially uniform illuminance distribution to the image pickup region. Namely, as shown in FIG. 9a, the radiation patterns of luminous fluxes obtained by light emission of the respective LED elements 23-1, 23-2, ..., 23-N are substantially spherical in the vicinity of the LED elements. However, the respective luminous fluxes are overlapped with those of adjacent LED elements to form a slightly uneven synthetic luminous flux. The unevenness in the luminous flux is smoothed with distance, whereby substantially even illuminance distribution is obtained at a portion in prescribed distance, i.e., on the surface of a fixed printed wiring board 10. FIG. 9b shows illuminance distribution in an illuminated region 27, wherein a region 28 having constant illuminance distribution is selected as an image pickup region 14. When the image pickup region 14 is thus supplied with constant illuminance distribution, photoelectric conversion outputs of the CCD image sensor are made uniform thereby to facilitate subsequent signal processing.

Although the light scattering type LED elements may be replaced by conventionally available LED elements having strong radiation pattern (since LEDs are mostly applied to pilot lamps, most of the conventional LEDs are formed by, e.g., resin materials containing semiconductor chips molded in the form of lenses to have radiation patterns) aligned in an array, light source points are required to be physically spaced while the respective ones of the light sources have sharp radiation patterns, and hence luminous fluxes are merely slightly overlapped in the direction of irradiation, whereby an uneven synthetic luminous flux is formed. Thus, the non-light-scattering type LED sources cannot supply uniform illuminance distribution in portions at short intervals, and require largely spaced distances. In this case, the number of arrays of the LEDs may be increased in order to obtain required illuminance, as hereinafter described.

Generally when, in addition to the above case, it is required to increase illuminance of the image pickup region 14 in view of the structure of the image pickup optical system and relation between the same and image pickup means, the LED element array is arranged, e.g., in two lines as shown in FIG. 6b. Further, the LED elements may be arranged in three lines or in the so-called zig-zag manner, if necessary.

With respect to luminance of the LED elements, bright type ones are employed in the embodiments, e.g., those of 100 mcd in axial luminance K in FIG. 8 (demand $I_F=200$ mA, ambient temperature $Ta=25°$ C.). A sufficiently practical lower limit of the axial luminance K is 50 to 60 mcd in view of the relation to the CCD image sensor. In recent years, various types of highly luminance LED elements have been developed, including that of superhigh luminance of 2000 mcd for optical communication, and the outputs from the CCD image sensor are increased with increase in the luminance K, leading to improvement in the signal-to-noise ratio. This means that the LED element array serving as the illumination source may further be small-sized, and, for example, the structure shown in FIG. 6b may be replaced by that shown in FIG. 6a. Such small-sized structure is particularly advantageous in the case where the entire image pickup apparatus is moved with the illumination source for scanning and inputting the patterns 11.

FIGS. 7a and 7b are illustrations showing LED arrays especially preferable as illumination sources for image pickup apparatuses. Each of the LED arrays is obtained by aligning a plurality of semiconductor chips $C_1, C_2, ..., C_n$ at equal picthes $p_1$ on a common stem (not shown) and integrally molding the same by transparent resin material 26'. Needless to say, the transparent resin material 26' preferably contains a light scattering agent. The semiconductor chips of the light emitting arrays are thus integrally assembled to form a light source, whereby the pitches $p_1$ and $p_2$ may be appropriately selected so that the radiation patterns may be sharp with respect to the array shaped light source formed by single-unit LED elements and the respective LED elements may not have high luminance. When, to the contrary, luminance of the semiconductor chips (LEDs) serving as the light source is high, efficiency of the illumination source is correspondingly increased. Further, the integrally formed structure remarkably facilitates design, manufacturing and handling of the device.

The respective structure of the aforementioned embodiments is adapted to overcome the problem of heat generation in the conventional lamp. Namely, an LED performs direct conversion of electricity into light, and further, operates at a low voltage and the demand thereof is remarkably small despite the high luminance. The LED is mechanically strong, resistant to vibration and by far durable in comparison with the conventional lamp, substantially requires no replacement, and is extremely easy to handle. Further, its luminous wavelength region is narrow and hence it requires no provision of a filter etc. for passing a specific wavelength region alone, which is required in case of the conventional lamp, while being remarkably stable as an illumination source since changes in the luminous power are small. Still further, the operation speed is high and the luminous power is immediately stabilized, whereby image pickup processing can be promptly performed. In addition, the illumination source can be formed at a low cost, leading to reduction in cost of the entire image pickup apparatus.

Description is now made on a preferable modification relating to the embodiment as shown in FIG. 5. Generally in inspection of defects in copper patterns of an etched printed wiring board, it is important in view of the signal-to-noise ratio of input circuit portion of the device and subsequent signal processing etc. to introduce, e.g., a glass epoxy base as the background and copper wire portions as patterns in finest possible optical contrast. Therefore, attention has been directed to luminous characteristics of LEDs as illumination source and spectral sensitivity of a solid state image sensor as image pickup means, in order to perform image pickup operation of copper patterns in excellent contrast.

In the modification, LEDs having peaks of light emission intensity in regions in conformity to spectral reflection characteristics of copper (pure copper) patterns are selected with respect to spectral luminous characteristics of the LEDs, while a CCD image sensor is selected from those having peaks of spectral sensitive characteristics in regions in conformity with the spectral reflection characteristics of copper, i.e., in the long-wavelength sides of visible light.

Figure 10:
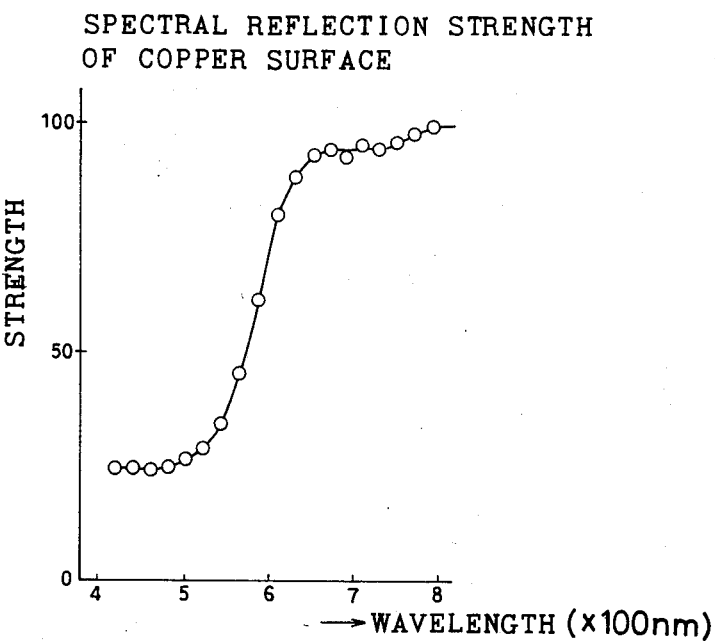
FIG. 10 is a graph showing spectral reflection strength of a copper foil surface having no strias.
Figure 11:
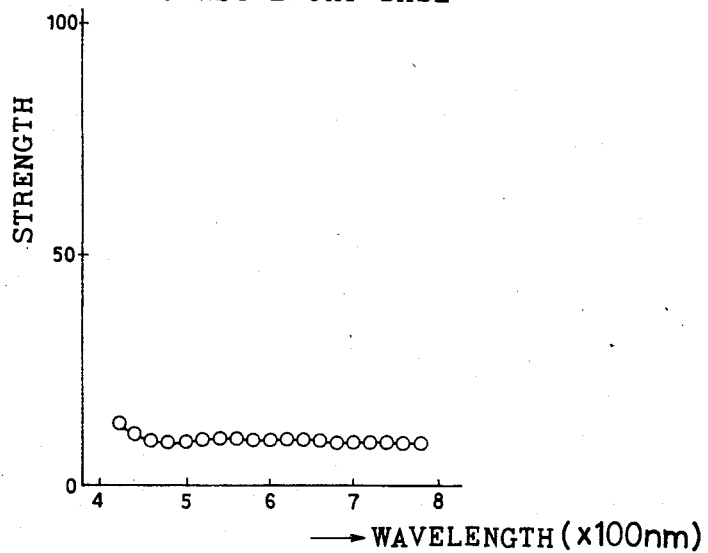
FIG. 11 is a graph showing spectral reflection strength of a glass epoxy material forming the base portion of a printed wiring board.

FIGS. 10 and 11 respectively show the results of definite investigation on spectral reflection strength characteristics of a copper surface of a printed wiring board and a glass epoxy base. As obviously understood from FIGS. 10 and 11, the contrast is remarkably excellent in the long-wavelength side in which the wavelength is over about 550 nm, particularly over 660 nm. Thus, the LEDs and the CCD image sensor have been selected to have peaks of spectral characteristics within the said range.

Figure 12:
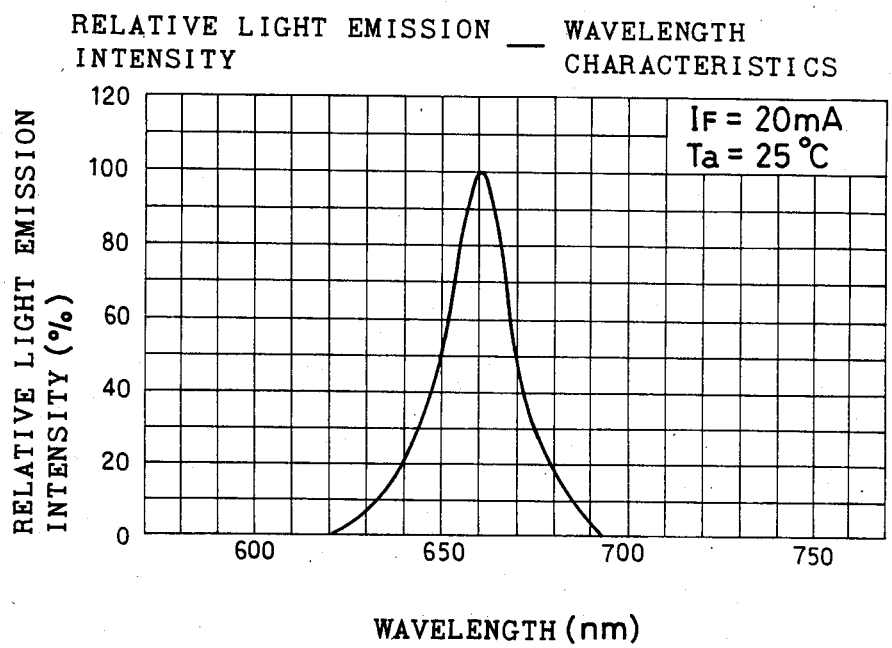
FIG. 12 is a graph showing relative light emission intensity-wavelength characteristics of a light emitting diode employed in the embodiment of the present invention.
Figure 13:
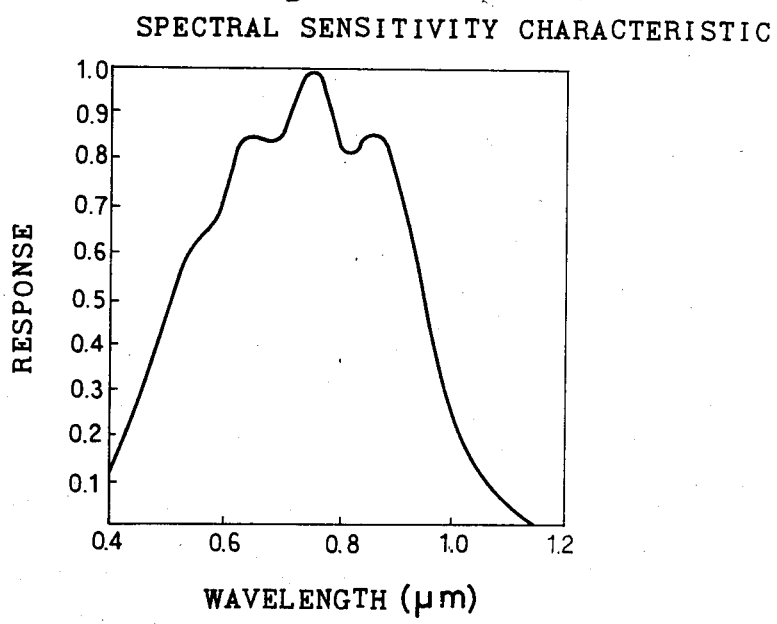
FIG. 13 is a graph showing the spectral sensitivity characteristic of a one-dimensional CCD image sensor employed in the embodiment of the present invention.

In concrete terms, the LEDs are implemented by those having peak luminous wavelength of about 660 nm as shown in FIG. 12, and more specifically, by GaAlAs red light emitting diodes of double hetero structure of, preferably, light scattering and highly luminant type. On the other hand, the CCD image sensor has been selected from those having peaks of spectral sensitivity characteristics around 700 nm as shown in FIG. 13.

Thus, the copper patterns serving as the object of image pickup can be easily discriminated with respect to the substrate base portion as the background, whereby stable image pickup outputs can be obtained while subsequent signal processing is simplified.

What is claimed is:

1. An image pickup apparatus for a printed wirng board comprising illumination source means for supplying constant irradiation light on the surface of a printed wiring board provided with copper patterns and a solid state image sensor for receiving light reflected by said surface of said printed wiring board through a lens thereby to output image pickup signals, said solid state image sensor comprising a one-dimensional CCD image sensor extending over said printed wiring board and having a light receiving surface set parallel to the surface of said board and opposed to said surface of said printed wiring board, said illumination source means being formed by a main illumination source arranged to reflect light specularly on said surface of said printed wiring board with respect to said light receiving surface of said solid state image sensor and a subsidiary illumination source arranged to reflect light diffusely on said surface of said printed wiring board with respect to said light receiving surface of said solid state image sensor thereby to supply said light receiving surface with scattering light diffusedly reflected by the surface of said copper patterns.

2. An image pickup apparatus for a printed wiring board in accordance with claim 1, wherein an optical axis of said lens focused on said light receiving surface of said solid state image sensor is in parallel with a normal line on said surface of said printed wiring board.

3. An image pickup apparatus for a printed wiring board in accordance with claim 1, wherein an optical axis of said lens focused on said light receiving surface of said solid state image sensor is coincident with an optical path of regularly reflected light from said main illumination source and in parallel with a normal line on said light receiving surface.

4. An image pickup apparatus for a printed wiring board in accordance with claim 1 or 3, wherein an incident angle of irradiated light from said main illumination source is less than 10° with respect to said printed wiring board.

5. An image pickup apparatus for a printed wiring board in accordance with claim 1, wherein said solid state image sensor has a peak of spectral sensitivity in a long-wavelength side of visible light to be in conformity with the spectral reflection characteristic of copper.

6. An image pickup apparatus for a printed wiring board comprising illumination source means for supplying constant irradiation light on the surface of a printed wiring board provided with copper patterns and a solid state image sensor for receiving light reflected by said surface of said printed wiring board through a lens thereby to output image pickup signals, a light receiving surface of said solid state image sensor being set to be opposed to said surface of said printed wiring board, said illumination source means being formed by a main illumination source consisting of a plurality of light emitting diodes and arranged to reflect light specularly on said surface of said printed wiring board with respect to said light receiving surface of said solid state image sensor and a subsidiary illumination source consisting of a plurality of light emitting diodes and arranged to reflect light diffusely on said surface of said printed wiring board with respect to said light receiving surface of said solid state image sensor thereby to supply said light receiving surface with scattering light diffusedly reflected by the surfaces of said copper patterns.

7. An image pickup apparatus for a printed wiring board in accordance with claim 6, wherein an optical axis of said lens focused on said light receiving surface of said solid state image sensor is in parallel with a normal line on said surface of said printed wiring board.

8. An image pickup apparatus for a printed wiring board in accordance with claim 6, wherein an optical axis of said lens focused on said light receiving surface of said solid state image sensor is coincident with an optical path of regularly reflected light from said main illumination source and in parallel with a normal line on said light receiving surface.

9. An image pickup apparatus for a printed wiring board in accordance with claim 6 or 8, wherein an incident angle of irradiated light from said main illumination source is less than 10° with respect to said printed wiring board.

10. An image pickup apparatus for a printed wiring board in accordance with claim 6, wherein said solid state image sensor has a peak of spectral sensitivity in a long-wavelength side of visible light to be in conformity with the spectral reflection characteristic of copper.

11. An image pickup apparatus for a printed wiring board in accordance with claim 6, 7, 8 or 10, wherein respective said light emitting diodes have peaks of light emission intensity in the long-wavelength side of visible light.

12. An image pickup apparatus for a printed wiring board in accordance with claim 9, wherein said solid state image sensor has a peak of spectral sensitivity in the long wavelength side of visible light and respective said light emitting diodes have peaks of light emission intensity in the long-wavelength side of visible light.

* * * * *